United States Patent
Do et al.

(10) Patent No.: US 10,466,676 B1
(45) Date of Patent: Nov. 5, 2019

(54) SYSTEMS AND METHODS FOR SHEARING ADJUSTMENT OF A DENTAL ALIGNER CUTTING TOOL

(71) Applicant: SmileDirectClub LLC, Nashville, TN (US)

(72) Inventors: Tuan Do, Nashville, TN (US); Ian Kitching, Nashville, TN (US)

(73) Assignee: SmileDirectClub LLC, Nashville, TN (US)

( * ) Notice: Subject to any disclaimer, the term of this patent is extended or adjusted under 35 U.S.C. 154(b) by 0 days.

(21) Appl. No.: 16/393,656

(22) Filed: Apr. 24, 2019

Related U.S. Application Data (60) Provisional application No. 62/830,858, filed on Apr. 8, 2019.

(51) Int. Cl.
| | |
|---|---|
| *G05B 19/402* | (2006.01) |
| *A61C 7/02* | (2006.01) |
| *A61C 7/08* | (2006.01) |
| *B23D 36/00* | (2006.01) |

(52) U.S. Cl.
CPC ....... *G05B 19/402* (2013.01); *B23D 36/0008* (2013.01); *A61C 7/02* (2013.01); *A61C 7/08* (2013.01); *G05B 2219/42195* (2013.01)

(58) Field of Classification Search
CPC ........ G05B 19/402; G05B 2219/42195; B23D 36/0008; A61C 7/02; A61C 7/08
See application file for complete search history.

(56) References Cited

U.S. PATENT DOCUMENTS

| | | |
|---|---|---|
| 9,943,386 B2 | 4/2018 | Webber et al. |
| 10,011,050 B2 | 7/2018 | Kitching et al. |
| 10,098,709 B1 | 10/2018 | Kitching et al. |
| 10,258,439 B1 | 4/2019 | Kitching et al. |
| 2006/0003292 A1 | 1/2006 | Lauren et al. |
| 2006/0199153 A1* | 9/2006 | Liu ............... A61C 8/0089 433/213 |
| 2008/0141534 A1* | 6/2008 | Hilliard ............... A61C 7/02 29/896.11 |
| 2008/0187887 A1 | 8/2008 | Lu et al. |
| 2008/0254402 A1* | 10/2008 | Hilliard ............... A61C 7/08 433/24 |
| 2008/0305454 A1 | 12/2008 | Kitching et al. |
| 2008/0306724 A1 | 12/2008 | Kitching et al. |
| 2009/0113714 A1* | 5/2009 | Greenberg ........... A61C 7/08 29/896.11 |

(Continued)

OTHER PUBLICATIONS https://www.youtube.com/watch?v=vsR0_wTR2a8.*

*Primary Examiner* — Ronald D Hartman, Jr.
(74) *Attorney, Agent, or Firm* — Foley & Lardner LLP (57) ABSTRACT

A system for adjusting a cutting tool includes a cutting system that includes a cutting tool that includes a tip configured to cut material thermoformed to a dental model. The cutting system is configured to determine, based on a cut line generated for the cutting tool to cut a dental aligner from material thermoformed onto a dental mold, a target tool vector defined by an angle of a tip of the cutting tool with respect to a surface of the dental model at the cut line, compare the target tool vector to a constraint of the cutting tool, and adjust a position of the tip of the cutting tool with respect to the cut line to compensate for the target tool vector being outside the constraint of the cutting tool.

20 Claims, 6 Drawing Sheets

(56) References Cited

U.S. PATENT DOCUMENTS

| | | |
|---|---|---|
| 2013/0122448 A1* | 5/2013 | Kitching ................ A61C 7/002 433/24 |
| 2013/0144422 A1* | 6/2013 | Choi ...................... A61C 1/084 700/119 |
| 2014/0315153 A1* | 10/2014 | Kitching ................ A61C 7/002 433/213 |
| 2015/0132707 A1 | 5/2015 | Huang et al. |
| 2016/0074138 A1 | 3/2016 | Kitching et al. |
| 2017/0100214 A1* | 4/2017 | Wen ....................... A61C 7/002 |
| 2017/0304023 A1 | 10/2017 | Tsai et al. |
| 2018/0092714 A1 | 4/2018 | Kitching et al. |
| 2018/0116762 A1* | 5/2018 | Kopelman ............. A61C 7/002 |
| 2018/0165818 A1 | 6/2018 | Tsai et al. |
| 2018/0177570 A1 | 6/2018 | Alauddin et al. |
| 2018/0304497 A1 | 10/2018 | Kitching et al. |
| 2018/0333226 A1* | 11/2018 | Tsai ......................... A61C 7/08 |
| 2019/0008612 A1 | 1/2019 | Kitching et al. |
| 2019/0102880 A1* | 4/2019 | Parpara .................. G06T 7/521 |
| 2019/0167384 A1* | 6/2019 | Borovinskih ............ A61C 7/08 |

* cited by examiner

SYSTEMS AND METHODS FOR SHEARING ADJUSTMENT OF A DENTAL ALIGNER CUTTING TOOL

CROSS-REFERENCE TO RELATED APPLICATIONS

This application claims the benefit of and priority to U.S. Provisional Patent Application No. 62/830,858, filed Apr. 8, 2019, the contents of which are incorporated herein by reference in its entirety.

BACKGROUND

The present disclosure relates generally to dental aligners. More specifically, the present disclosure relates to trimming or cutting dental aligners.

Dental aligners may be worn by a patient receiving orthodontic treatment. Some dental aligners are fabricated by thermoforming aligner material to a dental mold. After thermoforming the aligner material to a dental mold, the formed aligner is cut and removed from the dental mold so that the aligner can be worn by the patient.

SUMMARY

At least one embodiment relates to a method of adjusting a cutting tool. The method includes determining, based on a cut line generated for a cutting tool to cut a dental aligner from material thermoformed onto a dental model, a target tool vector defined by an angle of a tip of the cutting tool with respect to a surface of the dental model at the cut line. The method includes comparing the target tool vector to a constraint of the cutting tool. The method includes adjusting a position of the tip of the cutting tool with respect to the cut line to compensate for the target tool vector being outside the constraint of the cutting tool.

Another embodiment relates to a system for adjusting a cutting tool. The system includes a cutting system including a cutting tool. The cutting tool includes a tip configured to cut material thermoformed to a dental model. The cutting system is configured to determine, based on a cut line generated for the cutting tool to cut a dental aligner from material thermoformed onto a dental mold, a target tool vector defined by an angle of a tip of the cutting tool with respect to a surface of the dental model at the cut line. The cutting system is configured to compare the target tool vector to a constraint of the cutting tool. The cutting system is configured to adjust a position of the tip of the cutting tool with respect to the cut line to compensate for the target tool vector being outside the constraint of the cutting tool.

Another embodiment relates to a non-transitory computer readable medium storing instructions that, when executed by a processor, cause the processor to perform operations. The operations include determining, based on a cut line generated for a cutting tool to cut a dental aligner from material thermoformed onto a dental model, a target tool vector defined by an angle of a tip of the cutting tool with respect to a surface of the dental model at the cut line. The operations include comparing the target tool vector to a constraint of the cutting tool. The operations include adjusting a position of the tip of the cutting tool with respect to the cut line to compensate for the target tool vector being outside the constraint of the cutting tool.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, described herein are systems and methods for adjusting a cutting tool. A cutting system is configured to determine, based on a cut line generated for the cutting tool to cut a dental aligner from material thermoformed to a dental model, a target tool vector defined by an angle of a tip of the cutting tool with respect to a surface of the dental model at the cut line. The cutting system is configured to compare the target tool vector to a constraint of the cutting tool. The cutting system is configured to adjust a position of the tip of the cutting tool with respect to the cut line to compensate for the target tool vector being outside the constraint of the cutting tool.

Figure 1:
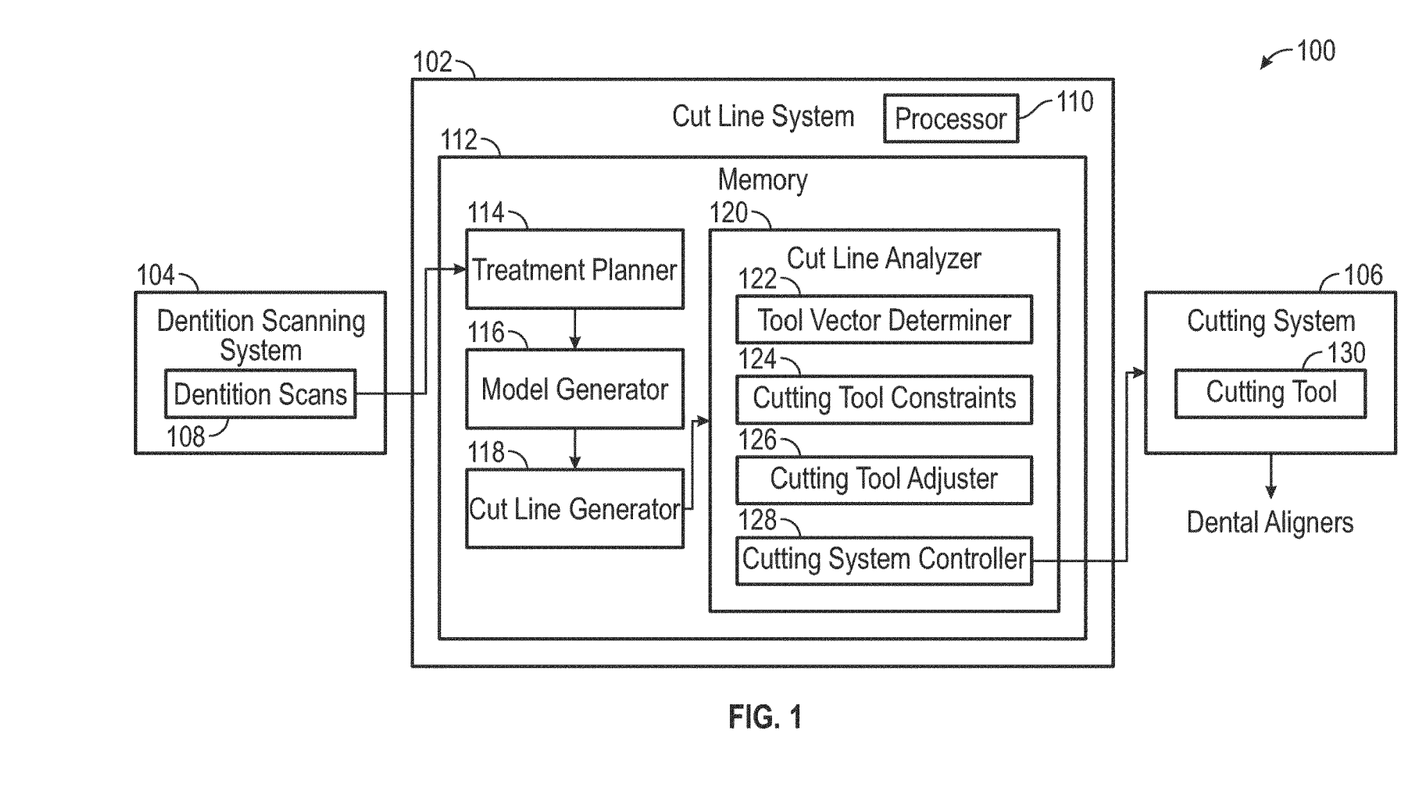
FIG. 1 is a block diagram showing a system for fabricating dental aligners, according to an illustrative embodiment.

Referring now to FIG. 1, an embodiment of a system 100 for fabricating dental aligners is shown. The system 100 is shown to include a cut line system 102, a dentition scanning system 104, and a cutting system 106. The dentition scanning system 104 includes any device, component, or group of devices or components configured to generate dentition scans 108. The dentition scans 108 may be digital scans of a physical dental impression (e.g., captured by a dental technician, a dentist, a user of a dental aligner). The dentition scans 108 may be direct scans of a patient's dentition. Hence, the dentition scans 108 may be direct scans of a patient's dentition captured by scanning the patient's dentition with a three-dimensional camera, or the dentition scans 108 may be indirect scans of the patient's dentition captured by scanning a physical model or impression of the patient's dentition. In either embodiment, the dentition scans 108 are three-dimensional representations of a patient's dentition. The dentition scans 108 may be used for fabricating a dental aligner, such as the dental aligner 800 shown in FIG. 8, as described in greater detail below.

In some implementations, the cut line system 102 may be embodied as or include a processing circuit which includes a processor 110 and memory 112. The processor 110 may be a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. The processor 110 also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function.

The memory 112 (e.g., memory, memory unit, storage device) may include one or more devices (e.g., RAM, ROM, EPROM, EEPROM, optical disk storage, magnetic disk storage or other magnetic storage devices, flash memory, hard disk storage, or any other medium) for storing data and/or computer code for completing or facilitating the various processes, layers and circuits described in the present disclosure. The memory 112 may be or include volatile memory or non-volatile memory, and may include database components, object code components, script components, or any other type of information structure for supporting the various activities and information structures described in the present disclosure. According to an illustrative embodiment, the memory 112 is communicably connected to the processor 110 via a processing circuit and includes computer code for executing (e.g., by the processing circuit or the processor 110) the processes described herein.

The memory 112 may store various modules or be comprised of a system of circuits. The circuits may include hardware, memory, and/or other components configured or implemented to execute various functions. The memory 112 may store a treatment planner 114, a model generator 116, a cut line generator 118, and a cut line analyzer 120. The treatment planner 114 may be a circuit designed or implemented to perform various functions corresponding to generating a treatment plan for the user's dentition (e.g., based on the dentition scans 108). The model generator 116 may be configured to generate a digital model based on the generated treatment plan. The digital model may be a three-dimensional representation of the user's dentition at various intervals (e.g., at the start of the treatment plan and at various intervals throughout the treatment plan). The cut line generator 118 may be configured to generate a cut line for cutting thermoforming material which has been thermoformed to a physical model which is cast, 3D printed, molded, created using Stereolithography, or otherwise formed based on the digital model. The cut line analyzer 120 may be configured to analyze the cut lines generated by the cut line generator 118 for shearing adjustment of the cutting tool 130, as described in greater detail below.

In various embodiments, the treatment planner 114 is configured to produce, generate, assemble, compile, or otherwise create a treatment plan for moving various teeth of a user's dentition. The treatment plan may be a series of movements for teeth of a user's dentition from a starting arrangement to an ending arrangement. The treatment plan may be generated by or through use of the treatment planner 114. In some embodiments, a dental technician or professional uses the treatment planner 114 to generate the treatment plan by manipulating individual teeth or groups of teeth shown in digital models based on the dentition scans 108. For instance, the treatment planner 114 may present digital models based on the dentition scans 108 from the dentition scanning system 104 to the dental professional, who then can manipulate various teeth within the dentition scans 108.

The treatment planner 114 is configured to generate various stages of the treatment plan to move the teeth from the starting position (e.g., their current position as represented within the dentition scan 108) to a final position selected or provided by the dental professional. In some embodiments, the treatment planner 114 is configured to create the treatment plan without the assistance of a dental professional. For instance, the treatment planner 114 may analyze the dentition scans 108 to align the teeth with a dental arch fitted to the teeth. The treatment planner 114 may then generate various stages of the treatment plan to move the teeth from the starting position to the final position.

The model generator 116 is configured to generate digital models of the user's dentition at the various stages of the treatment plan generated by or using the treatment planner 114. The model generator 116 generates a plurality of digital models including an initial digital model, a final digital model, and at least one intermediate digital model. The initial digital model corresponds to a first stage of the treatment plan. The final digital model corresponds to a final stage of the treatment plan. Each intermediate digital model corresponds to an intermediate stage of the treatment plan.

The cut line generator 118 is configured to generate a cut line for cutting aligner material thermoformed to a physical model corresponding to the digital model (e.g., generated by the model generator 116). Hence, the physical model may be used for manufacturing dental aligners 800 which move the user's teeth from the first stage to the intermediate stage(s) and then to the final stage. The dental aligners 800 may be formed by thermoforming a material to the physical models, then cutting the thermoformed material from the physical models along the cut line to create dental aligners 800. The cut line generator 118 may be configured to generate a cut line which is followed by a cutting tool 130 of the cutting system 106, as described in greater detail below.

Figure 8:
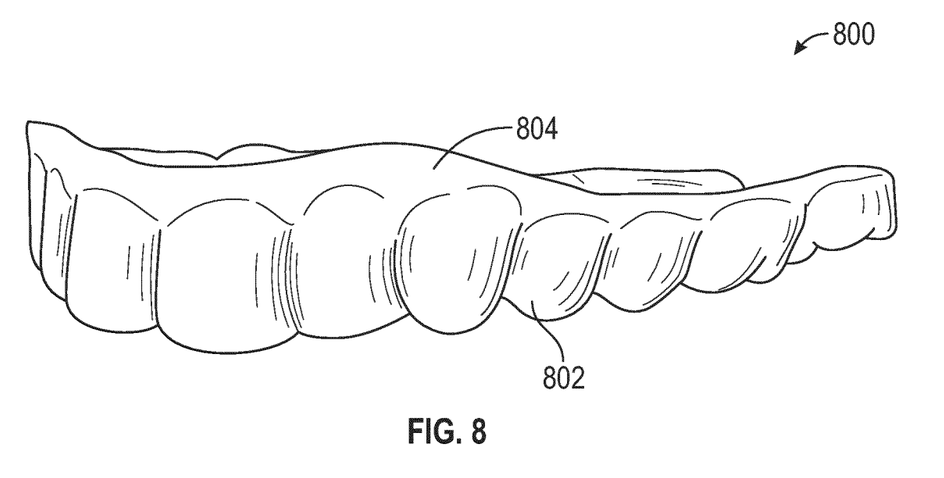
FIG. 8 is an illustration of a dental aligner fabricated using the system for manufacturing dental aligners of FIG. 1, according to an illustrative embodiment.

The user is provided a dental aligner 800 to be worn at each stage of the treatment plan for a predetermined duration (e.g., one week, two weeks, one month). The dental aligners 800 are constructed from a material thermoformed to a physical model and worn in the user's mouth. The dental aligners 800 apply a force on at least one of the user's teeth to move at least one tooth according to the treatment plan. In some embodiments, each stage includes more than one dental aligner 800 having the same shape but having a different thickness or being constructed of a different material (e.g., a harder or softer material). For example, the treatment plan can specify that the user wears the softest dental aligner 800 in a first sub-stage, followed by a dental aligner 800 of medium hardness, followed by the hardest dental aligner 800. In another example, the treatment plan can specify that the user wears the thinnest dental aligner 800 in a first sub-stage, followed by a dental aligner 800 of medium thickness, followed by a thickest dental aligner 800.

The dental aligners 800 are trimmed to fit comfortably within the user's mouth. The dental aligners 800 are trimmed to include representations of the user's teeth and a portion of the user's gums. The dental aligners 800 may be trimmed along a cut line using the cutting system 106. In some instances, a cutting tool 130 of the cutting system 106 may have physical constraints. For instance, the cutting tool 130 may only be capable of moving within a limited range. Hence, the cutting tool 130 may have a limited range of motion. In some instances, the cutting tool 130 may not be capable of following the cut line in certain portions (for instance, due to the position of the physical model with respect to the cutting tool 130, or due to the position of the cutting tool 130 within the cutting system 106). In such instances, the cut line analyzer 120 may adjust a position of the cutting tool 130 with respect to the cut line to accommodate for the constraints of the cutting tool 130, as described in greater detail below. Such embodiments may provide for a more accurate cut of the dental aligners 800 by ensuring that the cutting tool 130 follows the cut line, rather than shearing the dental aligners 800 at the cut line (which could cause fraying or an otherwise uneven cut of the dental aligners 800 due to the physical constraints of the cutting tool 130). The system 100 may adjust a position of the cutting tool 130 to compensate for physical constraints of the cutting tool 130 and thereby cause the cutting tool 130 to follow the cut line, or to substantially follow the cut line by cutting along the bottom or the top of the cut line. It is noted that, while this application is described with reference to trimming dental aligners 800, the systems and methods described herein may be adapted, used, applied or otherwise implemented to trim other dental appliances, such as retainers or mouth guards, and other objects where accurate cuts may be desirable. As such, the systems and methods described herein may have broad applicability, both in dental and orthodontic fields as well as in other fields.

Figure 2:
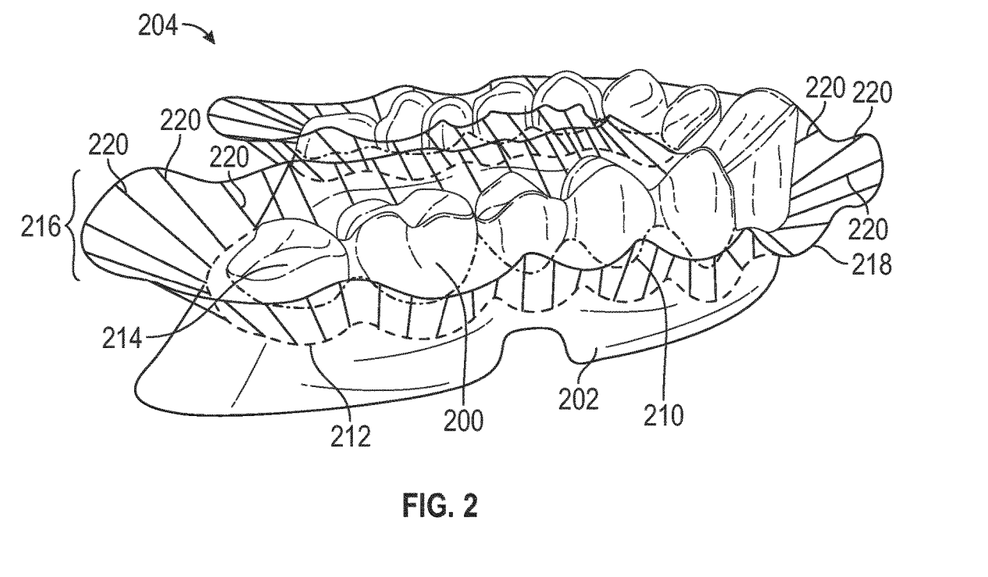
FIG. 2 is a back perspective view of a side of a digital model of a user's dentition, according to an illustrative embodiment.
Figure 3:
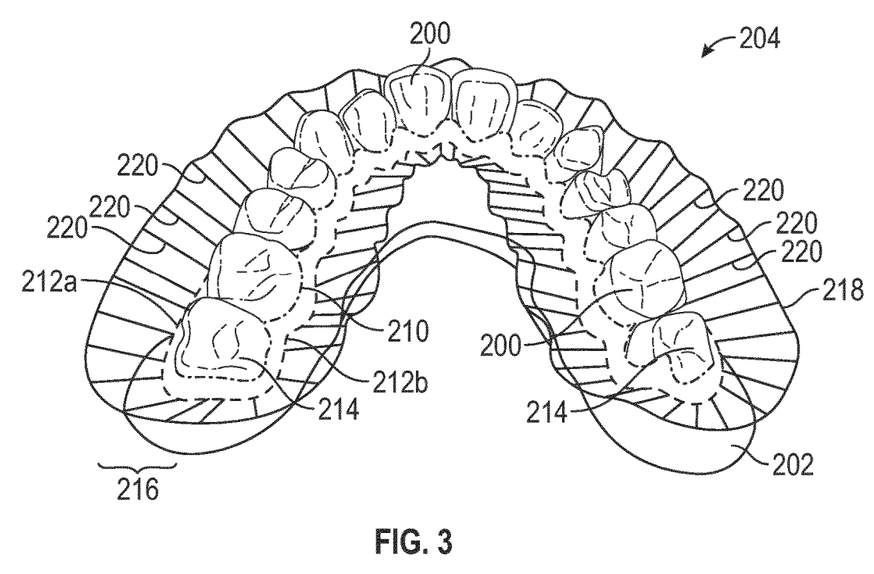
FIG. 3 is a rear perspective view of a digital model of a user's dentition, according to an illustrative embodiment.
Figure 4:
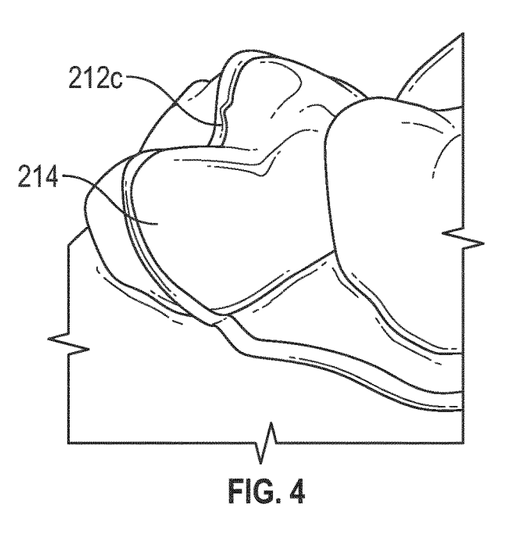
FIG. 4 is a back perspective view of rear molars of a digital model of a user's dentition, according to an illustrative embodiment.

Referring now to FIG. 2-FIG. 4, various views of a digital model 204 of a user's dentition are shown according to example embodiments. Specifically, FIG. 2 is a back perspective view of a side of a digital model 204 of a user's dentition, FIG. 3 is a rear perspective view of the digital model 204, and FIG. 4 is a back perspective view of rear molars of the digital model 204, according to illustrative embodiments. The cut line generator 118 may be configured to identify teeth 200 and gingiva 202 from the digital model 204 generated via the model generator 116. While described herein as teeth 200 and gingiva 202 with reference to the digital model 204, it is noted that the teeth 200 refer to a teeth portion 200 of the digital model 204 which correspond to teeth within the user's dentition, and gingiva 202 refer to a gingiva portion 202 of the digital model 204 which corresponds to gingiva within the user's dentition. The cut line generator 118 may be configured to identify a gingival line 210 for the digital model 204. The gingival line 210 is defined as the juncture or interface between the teeth 200 and gingiva 202. The cut line generator 118 may be configured to identify the gingival line 210 by identifying a location where the teeth 200 and gingiva 202 meet.

The cut line generator 118 is designed or implemented to define a cut line 212 for the dental aligner 800. The cut line 212 is a line or path which extends around the dental aligner 800 and defines a travel path along an outer edge 218 for a cutting tool 130 of the cutting system 106 to follow. The cutting tool 130 of the cutting system 106 may follow the outer edge 218 at a target tool vector 220. Each target tool vector 220 connects the outer edge 218 and cut line 212. The target tool vector 220 is angled with respect to a surface of the digital model 204. The cut line 212 may be defined a distance from the gingival line 210 in the gingiva 202 on the labial and lingual sides of the digital model 204. Hence, the cut line 212 includes a labial-side cut line 212a and a lingual-side cut line 212b. The labial-side cut line 212a and the lingual-side cut line 212b are connected at or around a rear molar 214. The labial-side cut line 212a and the lingual-side cut line 212b may be connected via a connecting cut line 212c which spans a center of mass for the rear molar 214 (as shown in FIG. 4) or wraps around the rear molar 214. In some embodiments, the connecting cut line 212c spans a different part of the rear molar 214 or spans a tooth other than the rear molar 214 (e.g., the second to last rear molar).

The cut line generator 118 is configured to define the cut line 212 in a manner similar to the cut line system described in U.S. patent application Ser. No. 16/292,779 for "Systems and Methods for Trimming Dental Aligners," filed Mar. 5, 2019, the contents of which are incorporated herein by reference in its entirety. As described in greater detail below, the cutting system controller 128 may control the cutting tool 130 (e.g., various actuators which manipulate or otherwise move the cutting tool 130) to move along the outer edge 218 to cut the dental aligner 800 (of FIG. 8) from the physical model with the thermoformed material positioned thereon. The dental aligner 800 includes a teeth portion 802 which interfaces with the user's teeth and a gingiva portion 804 which interfaces with the user's gingiva. The cut line 212 is located within the gingiva portion 804.

The cut line analyzer 120 is shown to include a cutting system controller 128. Once the cut line 212 is defined (and the position of the tip 502 of the cutting tool 130 is adjusted to compensate for constraints of the cutting tool 130, as described in greater detail below), the cutting system controller 128 is configured to control a cutting tool 130 of the cutting system 106 to cut a physical model 500 and thermoformed material thereon along the cut line 212 to prepare the dental aligner 800 for use. The cutting tool 130 may include a laser, a router, a CNC system, or other tool or system configured to cut a dental aligner 800. The cutting system 106 may include various actuators for controlling motion of the cutting tool 130. The cutting tool 130 may be configured to operate over various degrees of freedom, such as four, five, or six or more degrees of freedom. As described in greater detail below, the actuators or other components of the cutting system 106 may cause constraints to the cutting tool 130.

Figure 5A:
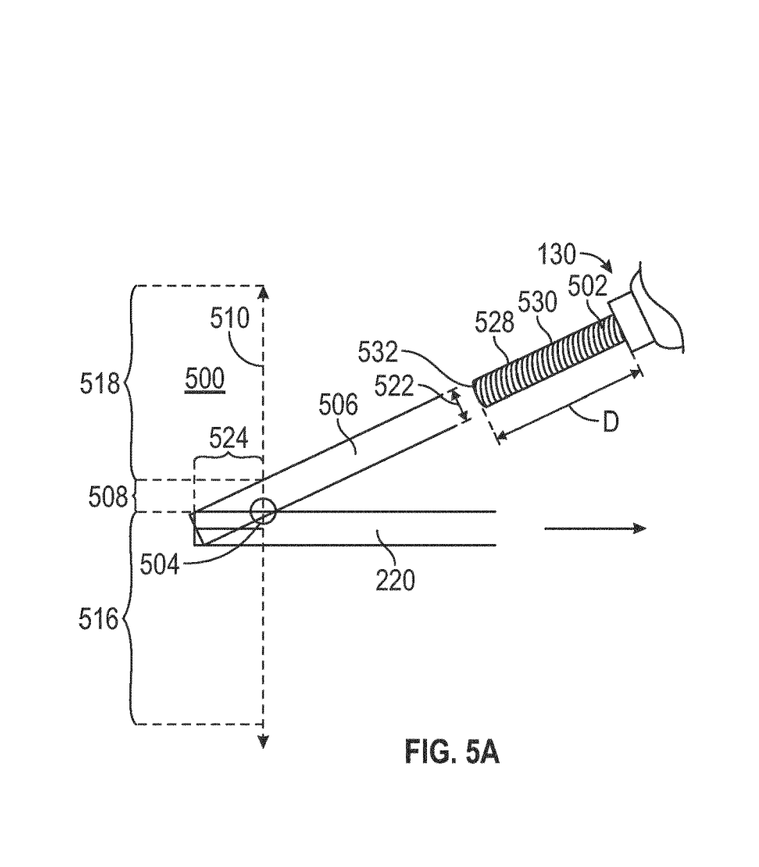
FIG. 5A and FIG. 5B are simplified side views of a cutting tool cutting a physical model corresponding to a digital model of a user's dentition, according to illustrative embodiments.
Figure 5B:
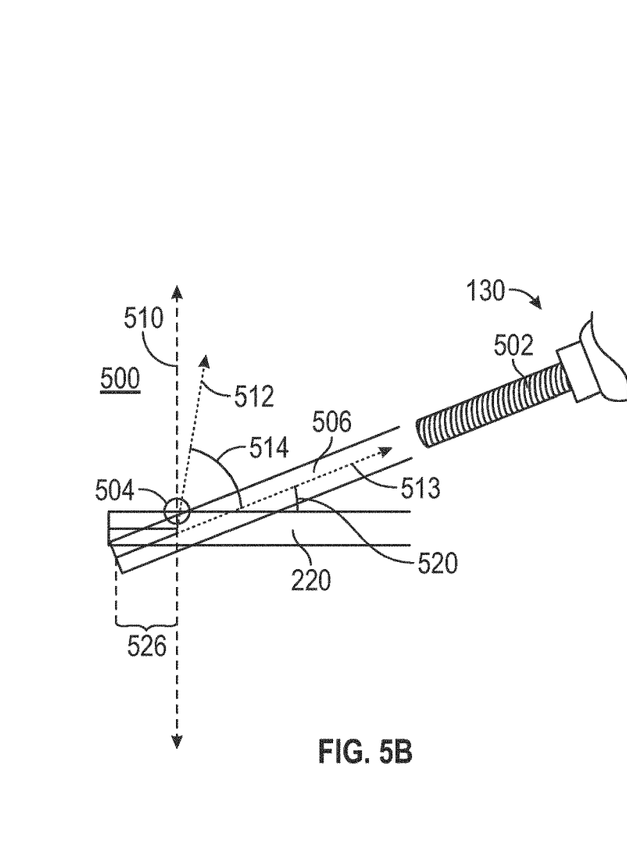

Referring FIG. 5A and FIG. 5B, simplified side views of cutting tool 130 cutting a physical model 500 corresponding to a digital model 204 of a user's dentition are shown according to illustrative embodiments. As described above, the cut line 212 extends around a physical model 500 and is used for cutting thermoforming material from the physical model 500 for fabricating the dental aligner 800. A tip 502 of the cutting tool 130 is configured to cut the physical model 500 and thermoforming material thereon. The cut line 212 may be formed of a plurality of points 504. The tip 502 of the cutting tool 130 cuts the physical model 500 at each point 504. In some instances, the target tool vector 220 is within the constraints of the cutting tool 130. In such instances, the cutting tool 130 is capable of following the target tool vector 220 to cut the physical model 500 and thermoforming material thereon along the cut line 212.

In some instances, the target tool vector 220 may be outside of the constraints of the cutting tool 130. In the example shown in FIG. 5A and FIG. 5B, the target tool vector 220 may be substantially perpendicular from the surface of the model 500. However, the cutting tool 130 may have physical constraints (such as, for instance, a limited angular range 514 in one or more directions) which cause the tip 502 of the cutting tool 130 to be incapable of being positioned perpendicular from the surface of the model 500. In FIG. 5A and FIG. 5B, the tip 502 of the cutting tool 130 may extend at an angle which is different from the target tool vector 220. The angle may be a maximum tool vector 506 for the cutting tool 130. The maximum tool vector 506 may be as close to the target tool vector 220 achievable by the cutting tool 130 within the constraints of the cutting tool 130. As shown in FIG. 5A, in implementations where the cut line analyzer 120 does not adjust a position of the tip 502 of the cutting tool 130, the tip 502 cuts an excess portion 508 of the model 500 which is offset from the point 504. As shown in FIG. 5B, where the cut line analyzer 120 adjusts a position of the tip 502 of the cutting tool 130 with respect to the cut line 212, the cut line analyzer 120 can compensate for the target tool vector 220 being outside the constraints (e.g., the angular range) of the cutting tool 130.

Figure 6:
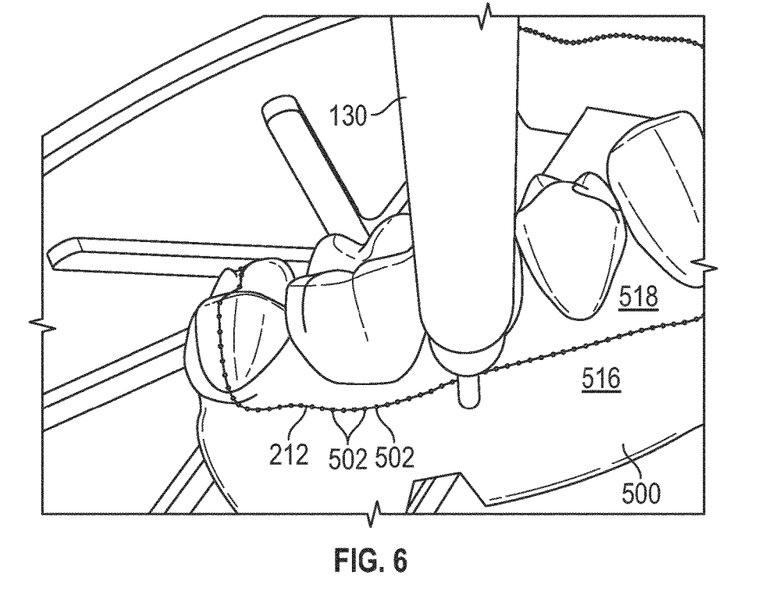
FIG. 6 is a perspective view of a cutting tool and physical model corresponding to a digital model of a user's dentition, according to an illustrative embodiment.

Referring now to FIG. 1, FIG. 5B and FIG. 6, the cut line analyzer 120 is configured to adjust a position (e.g., an orientation and/or location) of the tip 502 of the cutting tool 130 to compensate for the constraints of the cutting tool 130. Specifically, FIG. 6 depicts a perspective view of the cutting tool 130 and model 500, according to an illustrative embodiment. The cut line analyzer 120 is configured to adjust a position of the tip 502 of the cutting tool 130 with respect to the cut line 212. While shown as being embodied in the cut line system 102, in some embodiments, the cut line analyzer 120 may be embodied in the cutting system 106. The cut line analyzer 120 is configured to adjust the cutting tool 130 to more closely follow the cut line 212 by compensating for the movement constraints of the cutting tool 130. The cut line analyzer 120 may be configured to adjust the cutting tool 130 while the cutting tool 130 cuts the model. The cut line analyzer 120 may be configured to adjust various aspects of the travel path 216 and/or tool vector 220 prior to the cutting tool 130 cutting the model (e.g., preemptive adjustments of the cutting tool 130).

The cut line analyzer 120 is shown to include a tool vector determiner 122. The tool vector determiner 122 is configured to determine the target tool vector 220. The tool vector determiner 122 may be configured to determine the target tool vector 220 based on the travel path 216, outer edge 218, and cut line 212 for a given digital model 204. The tool vector determiner 122 may be configured to determine the target tool vector 220 by computing, for each point 504 of the cut line 212, a vector which extends between the point 504 and a corresponding point on the outer edge 218.

The cut line analyzer 120 is shown to include or access cutting tool constraints 124. Cutting tool constraints 124 may be the physical constraints of a particular cutting tool 130 or cutting system 106. In some embodiments, multiple cutting systems 106 can be used and operated at the same time to cut different dental aligners 800. In some cases, a first cutting system 106 can be different from a second cutting system 106 and can use a different cutting tool 130 than the other cutting system 106. Therefore, cutting systems 106 can have different constraints than other cutting systems 106. The cutting tool constraints 124 may be manually entered by an operator. The cutting tool constraints 124 may be downloaded or otherwise retrieved from a server or database associated with a manufacturer of the cutting tool 130. The cutting tool constraints 124 may be automatically generated by the cut line analyzer 120 by executing an initialization or calibration sequence when the cutting tool 130 is installed. The cutting tool constraints 124 may be different for various different cutting tools 130. The cutting tool constraints 124 may include a maximum angular range 514 of the cutting tool 130 in various directions (e.g., along various axes and combinations of axes).

The angular range 514 of the cutting tool 130 may be defined with respect to a pitch axis 510. The pitch axis 510 extends parallel to the surface of the model 500 or the cut point 504. In some embodiments, at each point 504 of the cut line 212, a pitch axis 510 may extend parallel to the surface of the model 500 and through the respective point 504. Hence, each point 504 may have a respective pitch axis 510. The tip 502 of the cutting tool 130 may move along a pitch angle with respect to the pitch axis 510. In some embodiments, the cutting tool 130 may be constrained to move between a minimum pitch angle 512 and maximum pitch angle 513, which together may define the angular range 514. The minimum pitch angle 512 may be, for instance, 5°, 8°, 10°, etc. The maximum pitch angle 513 may be, for instance, 70°, 75°, 80°, 85°, etc. The cut line analyzer 120 may be configured to store the angular range 514 as one of the cutting tool constraints 124 for the cutting tool 130. While angular range 514 is described as one possible constraint, the cutting tool constraints 124 may include other constraints, such as maximum or minimum yaw, minimum or maximum roll, and so forth.

The cut line analyzer 120 is shown to include a cutting tool adjuster 126. The cutting tool adjuster 126 may be design or implemented to selectively adjust a position of the cutting tool 130 with respect to the model 500. As described in greater detail below, the cutting tool adjuster 126 may be configured to adjust the position of the cutting tool 130 when the target tool vector 220 is outside of the angular range 514 of the cutting tool 130.

The cutting tool adjuster 126 is configured to determine whether the target tool vector 220 determined by the tool vector determiner 122 falls within the cutting tool constraints 124 for the cutting tool 130. In some embodiments, the cutting tool adjuster 126 is configured to determine whether the target tool vector 220 is within the angular range 514 of the cutting tool 130 (as indicated or reflected in the cutting tool constraints 124). The cutting tool adjuster 126 is configured to compare the target tool vector 220 to the angular range 514. The cutting tool adjuster 126 may be configured to determine whether the target tool vector 220 is greater than the minimum pitch angle 512 and less than the maximum pitch angle 513. Where the target tool vector 220 is within the angular range 514, the cutting tool 130 may be capable of following the cut line 212 at the target tool vector 220. In such instances, the cutting tool adjuster 126 may maintain a position of the tip 502 of the cutting tool 130 with respect to the cut line 212.

Where the target tool vector 220 is not within the constraints (e.g., the target tool vector 220 is outside the angular range 514 for the cutting tool 130), the cutting tool adjuster 126 may be configured to adjust a position of the tip 502 of the cutting tool 130 with respect to the cut line 212 to compensate for the target tool vector 220 being outside of the angular range 514 of the cutting tool 130. As described in greater detail below, the cutting tool adjuster 126 may shift the position of the tip 502 of the cutting tool 130 along (e.g., parallel to) the pitch axis 510 such that the cutting tool 130 cuts the aligner material thermoformed to the model 500 at or below the point 504 for the cut line 212, or substantially at or below the point 504 such that at least some portion of the tip 502 of the cutting tool 130 cuts the point 504 (e.g., a first portion of the tip 502 cuts the point 504 and a second portion of the tip 502 cuts above or below the point 504, and the second portion of the tip 502 is larger than the first portion of the tip 502).

In some embodiments, the cutting tool adjuster 126 defines a first portion 516 of the physical model 500 and a second portion 518 of the physical model 500 based on the digital model 204. The cutting tool adjuster 126 defines the first portion 516 and second portion 518 in relation to the cut line and a teeth portion of the digital model 204. The cutting tool adjuster 126 defines the first portion 516 as the portion of the physical model 500 which includes one or more tooth portions of the digital model 204. Hence, the second portion 518 may correspond to a gingiva portion of the digital model 204. The cutting tool adjuster 126 defines the first portion 516 and second portion 518 with respect to the cut line 212. The cutting tool adjuster 126 defines the first portion 516 as side of the physical model 500 which includes teeth 200. Stated another way, the cutting tool adjuster 126 may define the second portion 518 as the side of the physical model 500 which does not include teeth 200 (e.g., the portion of the model 500 which only includes gingiva 202). The cut line 212 separates the first portion 516 and second portion 518. In some embodiments, the cut line 212 may cross over one or more rear molars 214 (as shown in FIG. 4) via connecting cut line 212c. In such embodiments, the first portion 516 may include more teeth 200 or portions of teeth 200 than the second portion 518. As described in greater detail below, the cutting tool adjuster 126 may move the tip 502 of the cutting tool 130 along (e.g., parallel to) the pitch axis 510 toward the first portion 516 such that the tip 502 of the cutting tool 130 cuts the model 500 at (and below) the cut line 212.

In some embodiments, the cutting tool adjuster 126 is configured to determine an angular offset 520 between the target tool vector 220 and the maximum pitch angle 513 or the minimum pitch angle 512. The cutting tool adjuster 126 may be configured to select, from the maximum pitch angle 513 and minimum pitch angle 512, which of the maximum pitch angle 513 and minimum pitch angle 513 is closest to the target tool vector 220 for computing the angular offset 520. In the example shown in FIG. 5A and FIG. 5B, the maximum pitch angle 513 is closest to the target tool vector 220. The cutting tool adjuster 126 computes the angular offset 520 for determining an amount by which to adjust the position of the tip 502 of the cutting tool 130. The cutting tool adjuster 126 may adjust the position of the tip 502 of the cutting tool 130 in proportion to the angular offset 520.

In some embodiments, the cutting tool adjuster 126 is configured to identify various characteristics of the tip 502 of the cutting tool 130. Such characteristics may be stored or included in the cutting tool constraints 124. The cutting tool adjuster 126 may identify, for instance, a thickness 522 of the tip 502. The cutting tool adjuster 126 may be configured to use, at least, the thickness 522 in conjunction with other information and data for adjusting the position of the tip 502 of the cutting tool 130 with respect to the cut line 212.

In some embodiments, the tip 502 of the cutting tool 130 cuts into the model 500 at a target depth 524. The target depth 524 may change between a first cut and subsequent cuts. For instance, the model 500 may be used for generating a plurality of dental aligners 800. Each aligner may be thermoformed to the model 500 and subsequently cut from the model 500. The target depth 524 may change when each dental aligner 800 is cut from the model 500. For instance, the model 500 may be cut at a first target depth 524 for the first dental aligner 800, a second target depth 524 for the second dental aligner 800, a third target depth 524 for the third dental aligner 800, and so forth. Each target depth 524 may be different. The third target depth 524 may be greater than the second target depth 524, and the second target depth 524 may be greater than the first target depth 524. The target depths 524 of the cut may be defined within or a part of the cut line 212 (e.g., by the cut line generator 118). The cutting tool adjuster 126 may be configured to identify the target depth 524 of each cut for adjusting the position of the tip 502 of the cutting tool 130.

In some embodiments, the cutting tool adjuster 126 is configured to modify a cut depth 526 based on the angular offset 520. As shown in FIG. 5A and FIG. 5B, as the angular offset 520 increases, the cut depth 526 decreases. The cutting tool adjuster 126 is configured to modify the cut depth 526 (e.g., increase the cut depth) based on the angular offset 520. In some embodiments, the cutting tool adjuster 126 selectively modifies the cut depth 526. The cutting tool adjuster 126 may be configured to modify the cut depth 526 when the angular offset 520 causes the cut depth 526 to be greater than the target depth 524 (e.g., decrease the cut depth 526). The cutting tool adjuster 126 may maintain the cut depth 526 when the angular offset 520 causes the cut depth 526 to be less than the target depth 524. The cutting tool adjuster 126 may modify the cut depth 526 when the angular offset 520 is greater than a predetermined threshold. The predetermined threshold may correspond to instances where the difference between the target depth 524 and cut depth 526 is negligible. The cutting tool adjuster 126 may decrease or increase the cut depth 526 where the angular offset 520 is greater than the predetermined threshold.

The cutting tool adjuster 126 may be configured to determine an outermost edge 528 of the tip 502. The outermost edge 528 of the tip 502 is arranged along the side of the tip 502 which faces the second portion 518 of the model 500. The cutting tool adjuster 126 may be configured to determine a last contact point 530 along the outermost edge 528 which is to be located at the surface of the model 500 when the tip 502 of the cutting tool 130 cuts the model 500 at the target depth 524 and at the angular offset 520. The last contact point 530 may change based on the thickness 522 of the tip 502, the target depth 524 (and/or cut depth 526) of the cut, and/or the angular offset 520. For instance, as the angular offset 520 increases, the last contact point 530 may shift toward a base of the tip 502 since more of the tip 502 will contact the model 500 as the cutting tool 130 cuts the model 500. Similarly, as the target depth 524 or thickness 522 increases, particularly where the tip 502 is at least partially conical, the last contact point 530 may shift toward the base of the tip 502.

The cutting tool adjuster 126 is configured to compute the excess portion 508 based on the angular offset 520 and a distance D between the last contact point 530 and a first contact point 532 (e.g., a point on the tip 502 which first contacts the model 500). The cutting tool adjuster 126 may trigonometrically compute the excess portion 508 using a formula which uses the angular offset 520, and the distance D between the last contact point 530 and first contact point 532. In the example shown in FIG. 5B, the cutting tool adjuster 126 computes the excess portion 508 as excess portion 508=D sin(angular offset 520). In some embodiments, the formula changes as the target tool vector 220 deviates from 90° from the pitch axis 510. It will be appreciated that the example used herein is provided for simplicity and illustrative purposes only.

The cutting tool adjuster 126 is configured to adjust the position of the tip 502 of the cutting tool 130 based on the computed excess portion 508. The cutting tool adjuster 126 may move the tip 502 of the cutting tool 130 toward the cutting portion (e.g., parallel to the pitch axis 510) by the computed excess portion 508. By moving the tip 502 along the pitch axis 510 by the computed excess portion 508, the last contact point 530 may be located at the point 504 when the cutting tool 130 cuts the model 500 (e.g., rather than at a top of the excess portion 508 should the cutting tool 130 not be adjusted). As such, at least a portion of the tip 502 is located along the cut line 212 while a remainder of the tip 502 is located below the cut line 212 (e.g., within the first portion 516).

The cutting system controller 128 is configured to communicate signals to the actuators to control motion of the cutting tool 130. The cutting system controller 128 moves the cutting tool 130 to a starting position at the outer edge 218 and angles the cutting tool 130 with respect to the cut line 212 (e.g., toward the cut line 212 at the target tool vector 220 or at the position which compensates for the target tool vector 220 not being within the constraints of the cutting tool 130). The cutting system controller 128 is configured to control the cutting tool 130 to cut the model 500 along the cut line 212 following the cut line 212 at the outer edge 218. Following the dental aligner 800 being cut from the model 500, the dental aligner 800 may be cleaned, packaged, and shipped (e.g., either by itself or as part of a group of aligners) directly to a user. The user may wear the aligners to adjust the position of the user's teeth according to the treatment plan.

Figure 7:
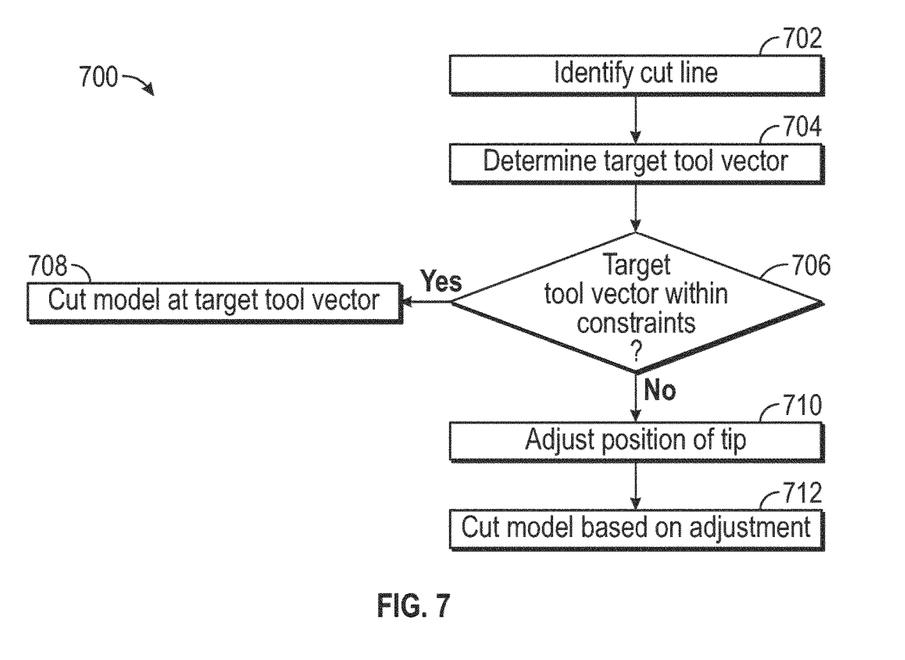
FIG. 7 is a flowchart of a method of a shearing adjustment of a cutting tool, according to an illustrative embodiment.

Referring now to FIG. 7, a flowchart of a method 700 of shearing adjustment of a cutting tool 130 is shown, according to an illustrative embodiment. The method 700 and corresponding description is one method that can be used for adjusting a position of the tip 502 of the cutting tool 130 for compensating for a target tool vector 220 being outside an angular range of the cutting tool 130. The cut line analyzer 120 is configured to use the method 700 or any other method to adjusting the position of the cutting tool 130. Furthermore, it is noted that the cut line analyzer 120 may perform such adjustments prior to the cut line 212 being followed by the cutting tool 130, or the cut line analyzer 120 may perform such adjustments as the cut line 212 is followed by the cutting tool 130. Hence, the position of the cutting tool 130 may be adjusted during a cutting operation or the outer edge 218 may be automatically adjusted to move the position of the cutting tool 130 prior to the cutting tool 130 cutting the model to generate the dental aligner 800.

At step 702, the cut line analyzer 120 identifies the cut line 212. In some embodiments, the cut line analyzer 120 identifies the cut line 212 for the thermoforming material thermoformed to the physical model 500 representative of a user's dentition. The cut line 212 may be followed by the cutting tool 130 configured to cut the thermoforming material. The cut line 212 separates a first portion 516 and a second portion 518 of model 500 corresponding to a first portion 516 and second portion 518 of the thermoforming material. Following cutting of the model 500 and thermoforming material, the second portion 518 of the thermoforming material may be the dental aligner 800.

At step 704, the cut line analyzer 120 determines a target tool vector 220. The cut line analyzer 120 may determine the target tool vector 220 based on the cut line 212 identified at step 702. The target tool vector 220 may be defined by an angle of a tip 502 of the cutting tool 130 with respect to a surface of the physical model 500 at the cut line 212. In some embodiments, the target tool vector 220 is defined within the cut line 212 generated by or using the cut line generator 118. In some embodiments, the cut line analyzer 120 calculates the target tool vector 220 by defining the target tool vector 220 based on points 504 for the cut line 212 and the outer edge for the cut line 212.

At step 706, the cut line analyzer 120 compares the target tool vector 220 with constraints of the cutting tool 130. The cut line analyzer 120 retrieves, determines, or otherwise accesses cutting tool constraints 124. The cutting tool constraints 124 may be stored locally. The cutting tool constraints 124 may be stored remotely (e.g., at a manufacturer of the cutting tool 130). The cutting tool constraints 124 may be determined by the cut line analyzer 120 by executing an initialization or calibration sequence for the cutting tool 130. The cutting tool constraints 124 may include, for instance, an angular range 514 along a pitch axis 510 for the cutting tool 130. Where the target tool vector 220 is within the constraints of the cutting tool 130, the method 700 proceeds to step 708. Where the target tool vector 220 is not within the constraints of the cutting tool 130, the method 700 proceeds to step 710.

At step 708, the cutting system controller 128 controls the cutting tool 130 to cut the model 500 at the target tool vector 220. The cutting system controller 128 may communicate signals to actuators of the cutting tool 130 to control motion of the cutting tool 130. The cutting system controller 128 moves the cutting tool 130 to a starting position at the outer edge 218 and angles the cutting tool 130 with respect to the cut line 212 (e.g., toward the cut line 212 at the target tool vector 220). The cutting system controller 128 is configured to control the cutting tool 130 to cut the model 500 along the cut line 212 following the cut line 212 at the outer edge 218.

At step 710, the cut line analyzer 120 adjusts a position of the tip 502 of the cutting tool 130. The cut line analyzer 120 may adjust a position of the tip 502 of the cutting tool 130 with respect to the cut line 212 to compensate for the target tool vector 220 being outside of the one or more constraints of the cutting tool 130. The cut line analyzer 120 may move the tip 502 of the cutting tool 130 toward the cutting portion along an axis (e.g., the pitch axis 510) such that an outermost edge 528 of the tip 502 is located at the cut line 212 while a remainder of the tip 502 is located within the first portion 516.

In some embodiments, the cut line analyzer 120 identifies a first contact point 532 for the tip and a last contact point 530 located along the outermost edge 528 of the tip. The cut line analyzer 120 may identify an angular offset 520 between the target tool vector 220 and a maximum pitch angle 513 for the cutting tool 130. The maximum pitch angle 513 may be one of the constraints which is compared to the target tool vector 220 at step 704. The cut line analyzer 120 may compute an excess portion 508 based on a distance D between the first contact point 532 and the last point 530 and the angular offset 520. The cut line analyzer 120 moves the tip 502 of the cutting tool 130 along the pitch axis 510 toward the first portion 516 by the excess portion 508 such that the last contact point 530 is located at the cut line 212 while the remainder of the tip 502 is located within the cutting portion.

In some embodiments, the cut line analyzer 120 modifies a cut depth 526. The cut line analyzer 120 modifies the cut depth 526 when the cut depth 526 is greater than a target depth 524. The cut line analyzer 120 modifies the cut depth 526 when an offset from the target depth 524 is greater than a threshold. The cut line analyzer 120 may identify a target depth 524 in which the cutting tool 130 is to cut into the thermoforming material and model 500 along the cut line 212. The cut line analyzer 120 may determine, based on the target tool vector 220 and adjustment of the position of the cutting tool 130, an offset from the target depth 524 following adjustment of the position of the tip 502 of the cutting tool 130. The cut line analyzer 120 may modify a cut depth based on the offset.

At step 712, the cutting system controller 128 controls the cutting tool 130 to cut the model 500 based on the adjustment performed at step 710. The cutting system controller 128 is configured to communicate signals to the actuators to control motion of the cutting tool 130. The cutting system controller 128 moves the cutting tool 130 to a starting position at the outer edge 218 and angles the cutting tool 130 with respect to the cut line 212 (e.g., toward the cut line 212 at the position which compensates for the target tool vector 220 not being within the constraints of the cutting tool 130). The cutting system controller 128 is configured to control the cutting tool 130 to cut the model 500 along the cut line 212 following the cut line 212 at the outer edge 218. In some embodiments, the adjustment is made while the cutting tool 130 is performing a cutting operation.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be X, Y, or Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the figures. It should be noted that the orientation of various elements may differ according to other exemplary embodiments, and that such variations are intended to be encompassed by the present disclosure.

The hardware and data processing components used to implement the various processes, operations, illustrative logics, logical blocks, modules, and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, flash memory, hard disk storage) for storing data and/or computer code for completing or facilitating the various processes, layers and circuits described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the systems and methods shown in the various exemplary embodiments are illustrative only. Additionally, any element disclosed in one embodiment may be incorporated or utilized with any other embodiment disclosed herein.

What is claimed is:

1. A method of adjusting a cutting tool, the method comprising:
   determining, based on a cut line generated for a cutting tool to cut a dental aligner from material thermoformed onto a dental model, a target tool vector defined by an angle of a tip of the cutting tool with respect to a surface of the dental model at the cut line;
   comparing the target tool vector to a constraint of the cutting tool; and
   adjusting a position of the tip of the cutting tool with respect to the cut line to compensate for the target tool vector being outside the constraint of the cutting tool.

2. The method of claim 1, wherein determining the target tool vector, comparing the target tool vector to the constraint, and adjusting the position of the tip of the cutting tool are performed as the cutting tool cuts the material.

3. The method of claim 1, wherein determining the target tool vector, comparing the target tool vector to the constraint, and adjusting the position of the tip of the cutting tool are performed prior to the cutting tool cutting the material.

4. The method of claim 1, wherein the cut line separates a first portion and a second portion of at least one of the material or the dental model.

5. The method of claim 4, wherein adjusting the position of the tip of the cutting tool comprises adjusting the tip of the cutting tool toward the second portion along an axis perpendicular to the cut line.

6. The method of claim 5, wherein adjusting the position of the tip further comprises:
   computing an excess portion based on the constraint of the cutting tool and the target tool vector; and
   adjusting the tip of the cutting tool toward the second portion by an amount of the excess portion.

7. The method of claim 1, further comprising:
   identifying a target depth that the cutting tool is to cut into the material and dental mold along the cut line;
   determining, based on the target tool vector and the adjustment of the position of the cutting tool, an offset from the target depth following adjustment of the position of the tip of the cutting tool; and
   modifying a cut depth based on the offset.

8. The method of claim 7, wherein the cut depth is modified based on the cut depth being greater than the target depth.

9. The method of claim 7, wherein the cut depth is modified based on the offset being greater than a threshold.

10. A system for adjusting a cutting tool, the system comprising:
    a cutting system comprising a cutting tool, the cutting tool comprising a tip configured to cut material thermoformed to a dental model, the cutting system configured to:
       determine, based on a cut line generated for the cutting tool to cut a dental aligner from material thermoformed onto a dental mold, a target tool vector defined by an angle of a tip of the cutting tool with respect to a surface of the dental model at the cut line;
       compare the target tool vector to a constraint of the cutting tool; and
       adjust a position of the tip of the cutting tool with respect to the cut line to compensate for the target tool vector being outside the constraint of the cutting tool.

11. The system of claim 10, wherein determining the target tool vector, comparing the target tool vector to the constraint, and adjusting the position of the tip of the cutting tool are performed as the cutting tool cuts the material.

12. The system of claim 10, wherein determining the target tool vector, comparing the target tool vector to the constraint, and adjusting the position of the tip of the cutting tool are performed prior to the cutting tool cutting the material.

13. The system of claim 10, wherein the cut line separates a first portion and a second portion of at least one of the material and the dental model.

14. The system of claim 13, wherein adjusting the position of the tip of the cutting tool comprises adjusting the tip of the cutting tool toward the second portion along an axis perpendicular to the cut line.

15. The system of claim 14, wherein adjusting the position of the tip further comprises:
    computing an excess portion based on the constraint of the cutting tool and the target tool vector; and
    adjusting the tip of the cutting tool toward the second portion by an amount of the excess portion.

16. The method of claim 10, wherein the cutting system is further configured to:
    identifying a target depth that the cutting tool is to cut into the material and dental mold along the cut line;
    determining, based on the target tool vector and the adjustment of the position of the cutting tool, an offset from the target depth following adjustment of the position of the tip of the cutting tool; and
    modifying a cut depth based on the offset.

17. The system of claim 16, wherein the cut depth is modified based on the cut depth being greater than the target depth.

18. The system of claim 16, wherein the cut depth is modified based on the offset being greater than a threshold.

19. A non-transitory computer readable medium storing instructions that, when executed by a processor, cause the processor to perform operations, the operations comprising:
    determining, based on a cut line generated for a cutting tool to cut a dental aligner from material thermoformed onto a dental model, a target tool vector defined by an angle of a tip of the cutting tool with respect to a surface of the dental model at the cut line;
    comparing the target tool vector to a constraint of the cutting tool; and
    adjusting a position of the tip of the cutting tool with respect to the cut line to compensate for the target tool vector being outside the constraint of the cutting tool.

20. The non-transitory computer readable medium of claim 19, wherein the cut line separates a first portion and a second portion of the dental model, and wherein adjusting the position of the tip of the cutting tool comprises:
    computing an excess portion based on the constraint of the cutting tool and the target tool vector; and adjusting the tip of the cutting tool toward the second portion by an amount of the excess portion.

\* \* \* \* \*